(12) United States Patent
Brown et al.

(10) Patent No.: US 6,423,528 B1
(45) Date of Patent: *Jul. 23, 2002

(54) HERPES SIMPLEX VIRUS-1 DELETION VARIANTS AND VACCINES THEREOF

(75) Inventors: Susanne M. Brown; Alasdair R. MacLean, both of Glasgow (GB)

(73) Assignee: The University Court of the University of Glasgow, Glasgow (GB)

( * ) Notice: Subject to any disclaimer, the term of this patent is extended or adjusted under 35 U.S.C. 154(b) by 0 days.

This patent is subject to a terminal disclaimer.

(21) Appl. No.: 09/335,039

(22) Filed: Jun. 16, 1999

Related U.S. Application Data

(63) Continuation of application No. 08/766,840, filed on Dec. 13, 1996, now Pat. No. 6,040,169, which is a continuation of application No. 08/439,042, filed on May 11, 1995, now abandoned, which is a continuation of application No. 08/094,047, filed as application No. PCT/GB92/00179 on Jan. 30, 1992, now abandoned.

(30) Foreign Application Priority Data

Jan. 31, 1991 (GB) .......................................... 91021261

(51) Int. Cl.⁷ ................................................. C12N 7/04
(52) U.S. Cl. .................................. 435/236; 435/235.1
(58) Field of Search .............................. 435/236, 235.1; 424/205.1, 231.1

(56) References Cited

U.S. PATENT DOCUMENTS

| | | | |
|---|---|---|---|
| 4,859,587 A | | 8/1989 | Roizman |
| 5,328,688 A | | 7/1994 | Roizman |
| 6,120,773 A | * | 9/2000 | Roizman ................. 424/205.1 |
| 6,172,047 B1 | * | 1/2001 | Roizman et al. ............... 514/44 |

FOREIGN PATENT DOCUMENTS

| | | |
|---|---|---|
| EP | 0 175 261 | 3/1986 |
| EP | 0 243 155 | 10/1987 |

OTHER PUBLICATIONS

MacLean et al., "Deletion and Duplication Variants Around the Long Repeats of Herpes Simplex Virus Type 1 Strain 17", Journal of General Virology, vol. 68, 1987, pp. 3019–3031.

MacLean et al., "Herpes Simples Virus Type 1 Deletion Variants 1714 and 1716 Pinpoint Neurovirulence–related Sequences in Glasgow Strain 17+ between, Immediate Early Gene 1 and the "a" Sequence", Journal of General Virology, vol. 72, Part III, Mar. 1991, pp. 631–639.

Taha et al., "A Variant of Herpes Simplex Virus type 2 strain HG52 with a 1.5 kb Deletion in RL Between 0 to 0.02 and 0.81 to 0.83 Map Units is Non–Neurovirulent for Mice", Journal of General Virology, vol. 70, 1989, pp. 705–716.

Roizman, "Introduction: Objectives of Herpes Simplex Virus Vaccines Seen from a Historical Perspective", Reviews of Infectious Diseases, 1991 13(Suppl. 11):S892–S894.

Bowie, et al., "Deciphering the Message in Protein Sequences: Tolerance to Amino Acid Substitutions", Science, vol. 247, pp. 1306–1310, Mar. 16, 1990.

Aurelian, "Herpes Simplex Viruses", In: Encyclopedia of Virology, vol. 2, Webster, R. & Granoff, A. Eds., Academic Press, New York, pp. 587–593 (1994).

Taha et al., J. Gen. Virol. 70: 3073–3078 (1989).

Kumar et al., Proc Natl Acad Sci 87.–1337–1341. 1990.

McGeoch et al., J. Gen. Virol. 69: 1531–1574 (1988).

Steiner et al. The EMBO J., 8(2): 505–511 (1989).

Mercadal et al., "Efficacy of the Herpes Simplex Virus Types 1 and 2 Mutant Viruses to Confer Protection Against Zosteriform Spread in Mice", Viral Immunology 6(1): 35–42 (1993).

Chou et al., "Mapping of Herpes Simplex Virus–1 Neurovirulence to $_{\gamma 1}34.5$, a Gene Nonessential for Growth in Culture", Science 250: 1262–1266 (1990).

Chou and Roizman, "The Terminal a Sequence of the Herpes Simplex Virus Genome Contains the Promoter of a Gene Located in the Repeat Sequences of the L Component", Journal of Virology 57(2): 629–637 (1986).

Chou and Roizman, "The Herpes Simplex Virus 1 Gene for ICP34.5, Which Maps in Inverted Repeats, is Conserved in Several Limited–Passage Isolated but Not in Strain 17syn+", Journal of Virology 64(3): 1014–1020 (1990).

Dolan et al., "Status of the ICP 34.5 Gene in Herpes Simplex Virus Type 1 Strain 17", Journal of General Virology 73: 971–973 (1992).

Davison et al, J. Gen. Virol. (1983); 64:1927–1942.

Lasner et al, J. Neuropathol. Exp. Neurol. (1996); 55(12):1259–1269.

* cited by examiner

*Primary Examiner*—Donna C Wortman
(74) *Attorney, Agent, or Firm*—Nixon & Vanderhye P.C.

(57) ABSTRACT

Novel Herpes simplex viruses and vaccines based on such novel HSV-1 strains are described. In particular, viruses having a deletion in the terminal portion of $R_L$ are provided. The virus can be further modified to express heterologous antigens and also engineered to overproduce HSV Light particles. This is achieved by incorporating a ts mutation into the UL26 gene.

10 Claims, 1 Drawing Sheet

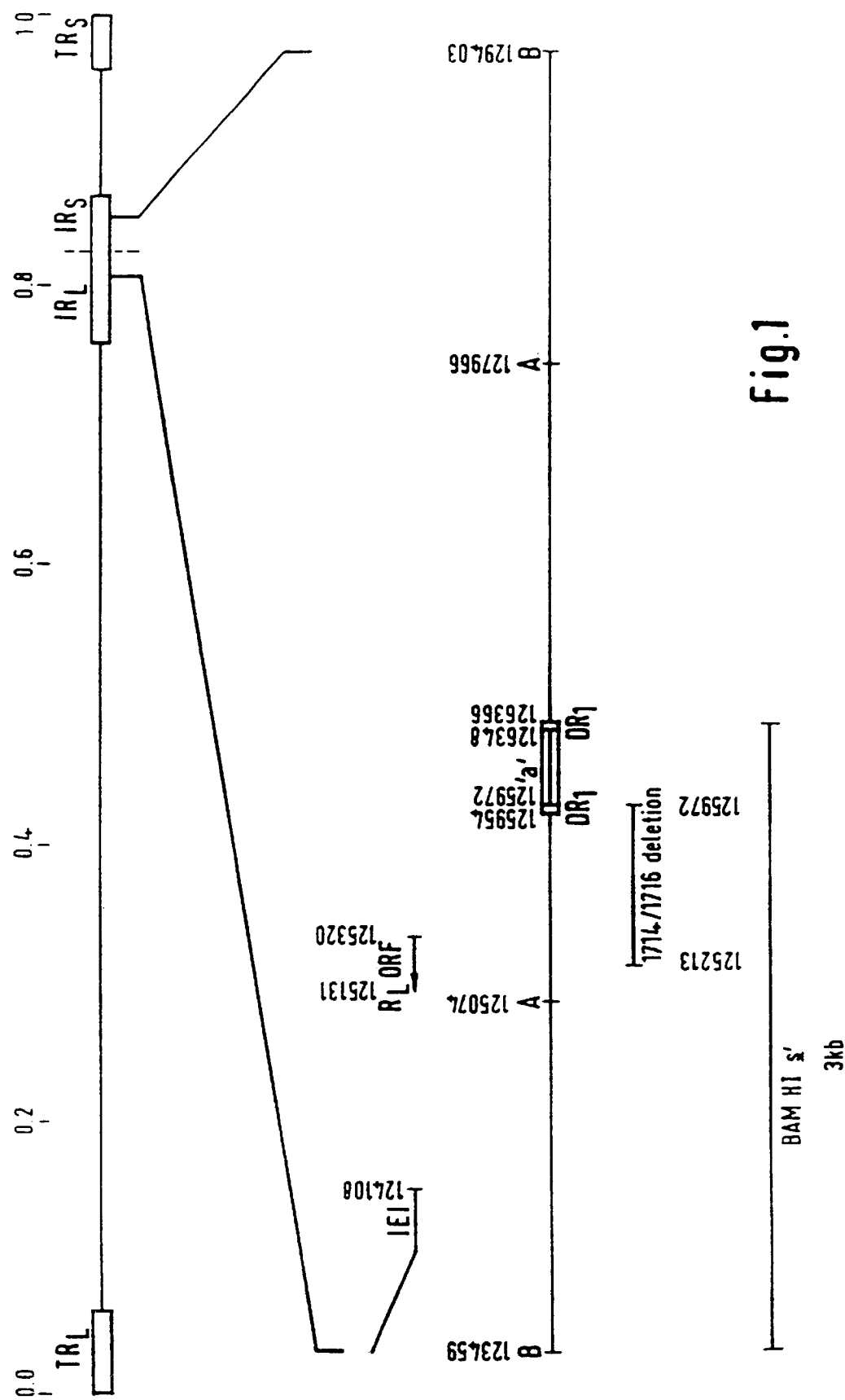

HERPES SIMPLEX VIRUS-1 DELETION VARIANTS AND VACCINES THEREOF

This application is a continuation of application Ser. No. 08/766,840, filed Dec. 13, 1996, now U.S. Pat. No. 6,040, 169; which is a continuation of Ser. No. 08/439,042, filed May 11, 1995 abandoned; which is a continuation of Ser. No. 08/094,047, filed Jul. 27, 1993 abandoned, which is a 371 application of PCT/GB/92/00179, filed Jan. 30, 1992 (abandoned).

This invention relates to variants of herpes simplex virus type 1 (HSV-1) which lack neurovirulence. Such variants are of value in the preparation of live attenuated vaccines for the prevention of HSV infections in humans.

Herpes simplex virus type 1 (HSV-1) and type 2 (HSV-2) are important human pathogens which infect more than 80% of the general population and cause recurrent mucocutaneous lesions. Following replication HSV enters the peripheral nervous system where active replication is turned off by an unknown mechanism. Thereafter a latent infection in neurons is established which persists for the life of the host. HSV can reactivate from the latent state to produce infectious lesions. HSV is responsible for a broad spectrum of clinical diseases ranging from relatively benign cutaneous lesions to fatal viral encephalitis.

A considerable amount of research has already been devoted to elucidation of the genetic organisation of both HSV-1 and HSV-2. The HSV-1 genome is a linear double stranded DNA molecule of approximately 152 kilobase pairs consisting of two components L and S. Each component consists of unique sequences $U_1$ and $U_s$, flanked by inverted repeats. The organisation of the HSV-2 genome is similar but not identical. For a detailed description of the genetic organisation of HSV-1 and HSV-2 (see McGeoch, 1987).

The identification of genes involved in viral pathogenicity and the elucidation of their precise functions is of fundamental importance to the understanding of the biology of herpes simplex virus (HSV). A number of variants of both HSV type 1 (strain 17) and HSV type 2 (strain HG52) with defined deletions in the unique and repeat sequences of both the long and short regions of the viral genome have already been isolated and characterised (Brown et al 1984, Harland and Brown 1985, Brown and Harland 1987, MacLean and Brown, 1987a and b, Harland and Brown 1989). Little is known, however, about the molecular mechanisms which regulate the neurovirulence of HSV. It has been shown that a deletion variant of HSV-2 strain HG52, termed JG2604, is avirulent on intracerebral inoculation of mice (Taha et al, 1989a). JH2604 has __ 1488 base pair deletion within both copies of the long repeat region of the genome [i.e. terminal long repeat ($TR_L$) and internal inverted long repeat ($IR_L$) regions].

An HSV-1 strain 17/HSV-2 strain HG52 recombinant (initially isolated in the Institute of Virology, Glasgow by Marsden et al, 1978), termed RE6, has also been reported to be avirulent in mice (Thompson et al 1989).

In HSV-1, inverted repeats of the L component designated ab and b'a' are each approximately 9 Kbp whereas those of the S component c'a' and ca, are each approximately 6.5 Kbp. A sequence shared by the inverted repeats of the L and S components is designed the 'a' sequence. This sequence has been reported (Chou and Roizman 1986) to contain the promoter-regulatory sequence and the transcription initiation sites for a diploid gene located in the b sequence of the inverted repeats of the L component. Working with HSV strain F these authors reported that there was a transcribed open reading frame (ORF) between the 'a' sequence and an immediate early gene designated IE1. By the use of antipeptide sera they were able to show that the ORF specified a protein designated ICP 34.5 (Ackermann et al 1986). Recently Chou and Roizman (1990) have reported that their now predicted ORF is conserved in 2 other HSV-1 strains analysed but not in Glasgow strain HSV-1 (17) syn+. It has been suggested by Chou et al (1990) that the neurovirulence locus of HSV-1 comaps with, and requires the expression of, ICP 34.5.

Surprisingly it has now been found that HSV-1 Glasgow strain 17 variants modified in the terminal portion of $R_L$ lack neurovirulence.

Such variants are incapable of replicating in CNS neurons, but are able, in mice to elicit a good immunological and cell mediated response since they are capable of replication in the peripheral tissue. This ability emphasises the vaccine potential of these strains.

According to the present invention there is provided an HSV-1 strain the genome of which is modified in the terminal portion of $R_L$ within Bam HI s (0–0.02 and 0.81–0.83 mu).

By Bam HI s it will be appreciated that what is meant is each copy of the approximately 3 Kb Bam HI s fragment of the HSV $R_L$ region.

The term ‘modified’ is used herein to denote disruption of the Bam HI s fragment by deletion of one or more nucleotides, insertion of additional nucleotides or any other alteration of the nucleotide sequence such as rearrangement, or substitution.

The HSV-1 strain may be a spontaneously isolated deletion variant of may be a wild type strain into which the desired modification has been introduced.

Such modifications in the HSV strain may be made by genetic manipulation, for example by site-directed mutagenesis, or by excision of a portion of the genome with or without replacement with a pre-prepared DNA cassette incorporating the required modification. Alternatively one may isolate naturally occurring HSV-1 variants, e.g. deletion variants.

Preferably the HSV-1 strain of the invention is a Glasgow strain 17 variant.

In one preferred aspect the HSV-1 strain is a strain in which at least 100 nucleotides in the Bam HI s' region between the Alu I site at 125074 np and 125972 np within the a sequence and its counterpart sequence in $TR_L$ have been deleted.

More preferably 0.5 to 3 kb of the Bam HI s' region and its counterpart in $TR_L$ is deleted, still more preferably about 0.7–2.5 kb is deleted.

In one specific example the HSV-1 variant is a strain designated 1714 which is a spontaneously occurring deletion variant of variant 1702 and lacks 759 bp within each copy of the Bam HI s fragment of the $R_L$ region as described hereinbelow, in which the deletion associated with non-neurovirulence is located between nucleotide positions 125213 and 125972.

Such a deletion removes one complete copy of the 18 bp $DR_1$ element of the ‘a’ sequence and terminates 1105 bp upstream of the 5' end of the immediate early gene 1.

In another specific example the HSV-1 variant is a variant designated 1716 in which the 759 bp deletion in variant 1714 has been introduced into the wild type Glasgow strain $17^+$.

In order to understand the invention more clearly reference may be made to FIG. 1 hereinbelow in which:

(a) Shows the HSV-1 genome (with map units marked) in the prototype orientation; and (b) Shows an expansion of BamHI k(s+g). The BamHI (B) and AluI (A) sites flanking the deletion in 1714/1716 are marked. All coordinates are based on the numbering of McGeoch et al (1988). Also indicated are the positions of the 5' end of IE1, the 'a' sequence, the $DR_1/U_b$ boundary in the 'a' sequence, a 189 bp conserved open reading frame between HSV-1 and HSV-2 ($R_L$ ORF) and the end points of the 759 bp deletion in 1714/1716. The deletion extends from the $DR_1/U_b$ boundary to remove the 5' 107 bp of the $R_L$ ORF.

The present invention further provides a whole virus vaccine comprising an HSV-1 strain according to the invention wherein such vaccine comprises an immunoprotective and non-toxic amount of the strain of the invention. Such vaccine may comprise the strain alone or in conjunction with other antigens and/or adjuvants.

Due to their non-pathogenic nature, the viruses of the present invention are exceptional candidates for further modification. For example they may be further modified so as to carry heterologous antigens. The virus can be engineered so as to express antigens from HSV-2, such as HSV-2 gD. Such a virus, elicits both antibody and CTL responses to both type 1 and type 2 virus and, moreover, enhances the overall immune response. Similarly other antigens from the other pathogens may be presented by the viruses of the present invention. For example, gene products from HCMV, VZV, EBV, HHV6, HHV7, and HIV as well as other envelope viruses may be presented.

Moreover, the virus of the present invention may be modified by introducing a mutation, typically a temperature sensitive mutation into the gene UL26a which encodes the capsid protein, P40 (Liu & Roizman 1991 a+b).

Such a mutation at non-permissive temperatures, (typically 38.5° C.) results in the overproduction of light particles; that is virus particles lacking the nucleocapsid and nucleic acid, and hence infectivity. J. of Gen Virology (1991) 72 p661 Szilagyi and Cunningham.

Accordingly the present invention provides for light particles derived from the viruses described herein.

In a further embodiment, the present invention provides herpetic virus light particles carrying a heterologous antigen. For example in one embodiment of the present invention HSV-1 1716 has been modified to express HSV-2 gD, and also modified to contain a temperature sensitive mutation in UL26a gene at 38.5° C.; this mutant over produces light particles containing HSV-2 gD. Other HSV-2 protein maybe incorporated into such a virus, in particular the HSV-2 gene products ICPO, ICP4 and Vmw 65 kD. Membrane proteins from other herpetic virus such as HCMV, VZV, EBV, HHV6, HHV7, and other enveloped virus such HIV-1 and HIV-2 maybe presented. For example gB from HCMV, gp120 from HIV-1 or HIV2 maybe incorporated into the virus Light particle. In theory any heterologous membrane protein which does not interfere with viral entry into the cell, can be carried by the light particles according to the invention.

Accordingly, the present invention provides a herpetic viral light particle carrying a heterologous antigen. In particular, the present invention provides a herpes simplex virus, preferably type 1, light particle carrying a heterologous antigen. An embodiment of this aspect of invention is HSV-1 1716, $gD_1^+$, $gD_2^+$, UL26a ts and light particles derived therefrom.

The Light particles of the present invention may be prepared by a modification of the method of Szilagyi & Cunningham (supra). Briefly cells are infected at 5 pfu/cell at the non-permissive temperature (npt) 38.5° C. and the supernatant virus harvested at 30 hours post infection. This preparation is centrifuged on a preformed 5–15% Ficoll (made in Eagle's medium) gradient for 2 hours at 12 K. The Light particle band is removed with a 26 G needle and pelleted at 20 K overnight in normal cell growth medium (Eagles).

The light particles of the present invention are useful for vaccine purposes. Accordingly in a further aspect of the present invention there is provided a vaccine comprising a light particle from a herpetic virus carrying a heterologous antigen. In a further aspect there is provided a vaccine comprising an HSV-1 viral light particle derived from a virus comprising a modification in the terminal portion of $R_L$ within BamH1 s (0–0.02 and 0.81–0.83 mu).

Alternatively, or in addition to the above mentioned modification(s), a virus of the present invention may be modified by introducing a mutation, typically a deletion, which renders the LAT promoter ineffective. Such a mutation adds a further level of safety, reducing both the frequency and rate of reactivation from latency.

Accordingly the present invention provides an HSV-1 virus modified in the terminal portion of $R_L$ within BamHI s (0–0.02 and 0.81–0.83 mu) and also modified to render the LAT promoter ineffective. Such a modified virus may be further modified so as to produce heterologous antigens such example HSV-2 gD, in the manner contemplated above. Moreover, additionally or alternatively to expressing a heterologous antigen, a temperature sensitive mutation maybe incorporated into the gene UL26a, so as to enable the overproduction of light particles and thus reduce the amount of potentially infective virus present. Such light particles may be separated from infective virus by Ficoll centrifugation of a viral particle. Normally, the ratio of heavy to Light particles in the Light particle band would be $1:10^3$, however where a mutation in UL26a has been incorporated, the ratio of heavy to Light particles is typically in the order of $1:10^6$.

The invention also provides a process for preparing a whole virus vaccine, which process comprises admixing the strain according to the invention with a suitable carrier or adjuvant.

For the preparation of a live attenuated vaccine, standard methodology may be used.

In a further aspect, the invention provides a method of treating HSV infection in humans, which method comprises administering to a human subject in need thereof an immunologically effective dose of the vaccine according to the invention.

The mode of administration of the vaccine of the invention may be any suitable route which delivers an immunoprotective amount of the strain or Light particles of the invention to the subject. However, the vaccine is preferably administered parenterally via the intramuscular or deep subcutaneous routes. Other modes of administration may also be employed, where desired, such as oral administration or via other parenteral routes, i.e., intradermally, intranasally, or intravenously.

The appropriate immunoprotective and non-toxic dose of such vaccine can be determined readily by those skilled in the art, i.e., the appropriate immunoprotective and non-toxic amount of the strain or Light particle of this invention contained in the vaccine of this invention may be in the range of the effective amounts of antigen in conventional whole virus vaccines. It will be understood, nowever, that the specific dose level for any particular patient will depend upon a variety of factors including the age, general health, sex, and diet of the patient; the time of administration; the route of administration; synergistic effects with any other drugs being administered; and the degree of protection being sought. Of course, the administration can be repeated at suitable intervals if necessary.

The following examples illustrate the invention.

EXAMPLES

METHODS

Cells

Baby hamster kidney clone 13 cells (BHK21/C13) (MacPherson and Stoker 1962) were propagated in Eagle's medium containing twice the normal concentration of vitamins and amino acids, 5% (V/V) tryptose phosphate broth and 10% (V/V) calf serum (ETC10).

Viruses

Virus stocks were grown and titrated in BHK21/C13 cells as previously described (Brown et al 1973). The parenteral HSV-1 strain was Glasgow strain 17 (Brown et al 1973). The variant 1702 devoid of the four normally occurring HSV-1 XbaI sites was the parental virus from which 1714 was isolated (MacLean and Brown 1987a).

Restriction enzyme analysis of virus genomes

Restriction enzyme analysis was carried out by a modification of the technique of Lonsdale (1979). BHK21/C13 cells were infected in the presence of $^{32}P_i$ in phosphate free Eagle's medium containing 1% (V/V) calf serum and incubated at 31° C. for 48 h. Viral DNA was extracted with SDS and phenol and ethanol precipitated. The DNA was treated with various restriction enzymes using the manufacturer's recommended conditions. Digests were analysed by electrophoresis on agarose gels of the appropriate concentrations (0.5–0.8%) in TBE buffer (89 mM-Tris, 89 mM boric acid, 2 mM sodium EDTA). Gels were air dried and exposed to Kodak XS1 film.

DNA—DNA Hybridisation

DNA fragments from restriction endonuclease digests were transferred from agarose gels to Hybond nylon membrane (Amersham) by the method of Southern (1975) and hybridised with random primed DNA prepared from Bam HI k (s+g) fragment cloned into PAT153. Hybridisation was performed at 65° C. in a hybridisation buffer containing 7% SDS and 0.5M NaP, pH7 for 16 h. No prehybridisation was performed. Filters were washed as described previously (Brown et al 1984).

Animal Inoculation

Three week old BALB/C mice (Bantin and Kingman) were inoculated intracranially with individual virus stocks. Mice were anaesthetised with ether and 0.025 ml of the appropriate virus dilution in phosphate buffered saline (PBS) 5% calf serum was inoculated into the central region of the left cerebral hemisphere. Four mice were inoculated with each virus at doses between $10^1$ and $10^7$ pfu/animal. The virus stocks were always retitrated on the day of inoculation to determine the precise titre inoculated. Mice were observed daily after inoculation and the $LD_{50}$ calculated according to the formula of Reed and Muench (1938) on the basis of death up to day 21. Brains were removed from animals which died post inoculation, homogenised, sonicated and the resulting suspension titrated on BHK/21/C13 cells. Virus plaques were picked and their restriction enzyme profiles determined as described.

Virus growth properties in vitro

BHK21/C13 ($2\times10^6$) cells were infected at a moi of 5 pfu/cell. Absorption was carried out for 45 min at 37° C. and after two washes with phosphate buffered saline containing 5% CS and addition of a 2 ml overlay of Eagle's medium containing 10% CS, incubation was continued at 37° C. Samples were harvested at 0,2,4,6,8,12,16 and 24 h and virus released by sonication was titrated at 37° C.

Thymidine kinase assay

The method used was a modification of that of Jamieson and Subak-Sharpe (1974). BHK21/C13 cells were mock infected or infected with wild type or mutant virus at a moi of 5 pfu/cell. After absorption for 1 h and incubation for 6 h at 37° C., the cells were scraped into cold PBS and pelleted. The pellet was resuspended in lysis buffer (20 mM Tris-HCl pH 7.5, 2 mM $MgCl_2$, 10 mM NaCl, 0.5% V/V Nonidet P40, 6.5 mM 2 mercaptoethanol) maintained on ice for 5 min, mixed briefly and replaced on ice for a further 5 min. The samples were centrifuged and the supernatant retained. 5 µl of extract was mixed with the reaction buffer in a total volume of 50 µl (0.5M $Na_2PO_4$ pH6, 100 mM $MgCl_2$, 2 mM dTTP, 100 mM ATP, 5 µl aqueous $Me^3H$ thymidine 1 mCi/ml). After incubating for 1 h the reaction was stopped by the addition of 10 µl of 100 mM EDTA and 1 mM thymidine. The samples were heated for 3 min at 100° C. and placed on ice for 3 min. After centrifugation, the supernatant was spotted onto DE81 discs which were washed 3 times (10 min each at 37° C.) with 4 mM ammonium formate pH 6.0 and 10 µM thymidine. After a further 2 washes with ethanol, the discs were dried and radioactivity due to $^3H$ thymidine was determined.

Introduction of the deletion into wild type Glasgow strain 17

To introduce the 1714 deletion into wild type strain 17, the cloned novel BamHI k fragment of 1714 was linearised with BamHI and cotransfected at a 1,2,5,10 and 20 fold molar excess with intact DNA from $17^+$. Resulting individual plaques were isolated and their DNA analysed by the method of Lonsdale (1979). Virus which appeared to have acquired the deletion was plaque purified a further 3 times before growing a virus stock.

Sequence Analysis

The novel BamHI k fragment of 1714 was cloned into the BamHI site of pGEM 3z using standard procedures (Maniatis 1982). Positive clones were identified by restriction enzyme analysis and confirmed by Southern blotting total HSV-1 DNA and using random primed DNA from the positive clones. Further restriction enzyme analysis confirmed that the deletion was approximately 800 bp in size and was within a 2.8 kg AluI fragment. This fragment was eluted from a gel, digested with SmaI and several small fragments were subcloned into M13mp8. Single stranded template DNA was prepared and sequenced using $^{35}S$ labelled dATP by the method of Sanger et al (1980). The sequencing products were run on a single concentration 6% acrylamide, 1×TBE, 8.3M urea gel.

Latency studies

Three week old BALB/C mice (Bantin & Kingman) were inoculated in the right rear footpad as described previously (Clements & Subak-Sharpe 1983, 1988). At the time of inoculation the virus was titrated on BHK21/C13 cells to confirm the precise dose administered. For each virus a series of 100 fold dilutions was inoculated and mice were examined and scored daily for clinical symptoms. Mice surviving 6 weeks were examined for the presence of latent virus. The mice were killed, dissected and the two lowest thoracic, six lumbar and the upper two sacral ganglia were removed from the inoculated side, placed in culture medium and screened for release of infectious virus every second day by transferring the culture medium to control BHK21/C13 cells. The inoculated BHK21/C13 cells were incubated at 37° C. for 2 days before staining and examining for the presence of virus plaques or cpe.

Example 1 a) Isolation and genome analysis of the variant 1714

To study recombination in HSV we have constructed viruses devoid of certain restriction enzyme sites which are to be used as unselected markers (Brown et al 1984; Harland and Brown 1985; MacLean and Brown 1987c). The HSV-1 strain 17 mutant 1702 (MacLean and Brown 1987c) (devoid of the four HSV-1 XbaI sites and TK⁻) was the parental virus used to remove various HindIII sites by site directed mutagenesis. DNA from the virus isolate H1 derived from 1702 but lacking the 0.91 mu HindIII site was cotransfected with a mutagenised plasmid devoid of the 0.18 mu HindIII site. A large number of resulting progeny plaques were picked and their DNA subjected to restriction enzyme analysis. In addition to successfully isolating a desired mutant in which the 0.18 mu HindIII site had been lost, a virus (1714) with aberrant RE profiles unrelated to the loss of HindIII sites was detected.

On KpnI digestion of 1714 DNA KpnI r ($2.4 \times 10^6$ mw) was found to be missing and a novel band of about $1.9 \times 10^6$ was seen running between fragments t and u. KpnI r is the terminal portion of $R_L$ (0–0.025 mu and 0.805–0.83 mu) and forms the joint fragments a(r+j) and e(r+k). It can be seen that the 1714 e fragment is running marginally faster than its equivalent wild type fragment but no alteration in a which runs at the top of the gel can be seen. Similarly HpaI m ($3.6 \times 10^6$ mw) was missing and a novel band of approx $3.1 \times 10^6$ mol wt was detectable running below n. HapI m (0–0.036 mu and 0.79–0.83 mu) forms the joints a(m+c) and d(m+g) which can be seen in 1714 running marginally faster than 17⁺. On BamHI digestion of 1714 DNA, BamHI s ($1.95 \times 10^6$ mw) is missing and a new band appears to be running below u/v with a mol wt of about $1.45 \times 10^6$. The BamHI s containing joint k (s+g) is also not detectable but a novel band with a mol wt of $3.5 \times 10^6$ presumed to be the deleted joint is seen below l.

Taken together, the restriction enzyme profiles indicated that 1714 was deleted in both copies of the terminal portion of $R_L$ between 0–0.095 mu and 0.81–0.83 mu. The size of the deletion was estimated to be between 600–800 bp.

To substantiate the loss of sequences in both copies of $R_L$, Southern blot analysis of 1714 DNA was carried out. 17⁺ and 1714 DNA were digested with BamHI and transferred to a nitrocellulose membrane. The BamHI k fragment (s+g) of 17⁺ DNA was random primed and hybridised to the digested DNA. It was found that in the 17⁺ track, the probe hybridised to k, g and s. In 1714 the probe failed to hybridise to k but hybridised to a novel k, to a novel k with additional 'a' sequences and to g. There was no hybridisation to s but to a novel s running below it. Incorporation of a size-ladder demonstrated the deletion to be about 800 bp. This result unambiguously demonstrates that 1714 was deleted in both copies of $R_L$ and that the deletion was contained within BamHI s.

b) Sequence Analysis

The BamHI k joint fragment (s+g) of HSV-1 strain 17 is located between nucleotide positions (n.p.) 123459 and 129403 (McGeoch et al 1988). In 1714 the BamHI k fragment is deleted by about 800 bp. This novel BamHI k of 1714 was cloned into the BamHI site of pGEM. Further restriction analysis indicated that the deletion lay within an AluI fragment (125074–127966 n.p.) which in the deletion variant 1714 was approximately 2.1 kb in size compared to the wild type 2.9 kb fragment. This AluI fragment from 1714 was eluted from an agarose gel, redigested with SmaI and the resulting subfragments were cloned into M13mp8. Dideoxysequencing of the SmaI fragments identified the deletion as being 759 bp in length and located between nucleotide positions 125213 and 125972. From the remaining SmaI fragments sequenced, no other mutations were detected. The only precisely defined gene in $R_L$ is IE1 whose 5' end in $IR_L$ is located at 124108 n.p. i.e. 1105 bp downstream of the deletion. The $IR_L/IR_S$ 'a' sequence in HSV-1 strain 17 starts at nucleotide position 125954. In 1714 one complete 18 bp DRI element (AGCCCGGGCCCCCCGCGG) of the 'a' sequence has been precisely removed.

Example 2 a) Neurovirulence of the deletion variant 1714 for Balb/c mice

We have previously shown that the deletion variant JH2604 of HSV-2 strain HG52 is non-neurovirulent for Balb/c mice with an $LD_{50}$ value of $>10^7$ pfu/mouse compared to $<10^2$ pfu/mouse for the wild type virus. Sequence analysis of JH2604 demonstrated that a 1488 bp sequence within the terminal portion of the genome long repeat (between 0–0.02 mu and 0.81–0.83 mu) conferred neurovirulence on strain HG52.

As 1714 had a deletion in the equivalent parts of the HSV-1 genome, experiments to determine the neurovirulence of 1714 compared to its parent 1702 and to 17⁺ by estimating their $LD_{50}$ values in Balb/c mice were carried out. Twenty five μl aliquots of different doses of 17⁺, 1702 and 1714 were inoculated into the left cerebral hemisphere of 3 week old Balb/c mice. Deaths from encephalitis were scored up to day 21 post inoculation and the results are shown in Table 1. The elite laboratory stock of 17⁺ showed an LD50 value of $<10^{1.5}$ pfu/mouse. The mutant 1702, although tk negative (MacLean and Brown 1987a) gave a marginally higher $LD_{50}$ value of $5 \times 10^2$ pfu/mouse. With 1714 no animals died with an inoculum of $10^6$ pfu but 3/4 died with $10^7$ pfu giving an $LD_{50}$ value of $7 \times 10^6$ pfu/mouse. Thus the deletion variant 1714 was at least $2 \times 10^4$ fold less neurovirulent than the parental 1702 virus and at least $7 \times 10^5$ fold higher than the wild type 17⁺. Single plaques were isolated from the brains of 1714 infected mice which had died and the DNA of the plaque isolates was digested with restriction enzymes. The RE profiles were identical to that of 1714, indicating no wild type contamination. The particle:pfu ratios of 72:1 for 17⁺ and 58:1 for 1714 are comparable and fall within the normal range of values for HSV-1.

b) Growth of 1714 in vivo

The HSV-2 (HG52) variant JH2604 was shown to be avirulent; failed to replicate in mouse brain and produced no necrotising encephalitis (Taha et al 1990). To determine whether the absence of neurovirulence of 1714 was also due to the failure of replication in mouse brain, samples of 17⁺ ($10^2$ pfu), 1702 ($10^2$ pfu) and 1714 ($10^5$ pfu) were inoculated into the left cerebral hemisphere of 3 week old Balb/c mice. At various times post inoculation 2 mice (per virus) were killed, their brains removed and frozen at −70° C. The brain tissue was homogenised, the resulting suspension sonicated and the progeny virus assayed by plaque titration on BHK21/C13 cells at 37° C. The results showed that for the parental strain 17, there was exponential growth of virus between 12 h post inoculation and day 6, reaching a final titre of $8 \times 10^6$ pfu/brain. Likewise with 1702 there was virus detectable 24 h post inoculation and exponential growth reaching a titre of $8 \times 10^4$ pfu/brain by 6 days. In the 1714 infected animals which had received an input dose of $10^5$ pfu, $2 \times 10^3$ pfu could be detected immediately post inoculation. No replication was detectable and the input virus declined until by 3 days post inoculation were was no assayable virus (<10 pfu).

c) Growth of 1714 in vitro

The variant 1714 grows to high titre ($>10^9$ pfu) by multicycle growth following low moi in BHK21/C13 cells. The stock gives equivalent titres when assayed at 31° C., 37°

C., and 38.5° C. To determine its growth pattern, single cycle growth experiments were carried out in BHK21/C13 cells at 37° C. The results showed that 17⁺ and the 1702 and 1714 variants grew equally well giving equivalent final yields. The normal single cycle growth pattern of 1714 indicates no impairment at any stage in its replicative cycle in BHK21/C13 cells.

The determine whether the virus was host restricted, 24 h yield experiments were carried out in a range of cell lines infected at a moi of 5 pfu/cell. The cell lines used were BHK/C13 (hamster), BSC1 (monkey), Vero (monkey), MDCK (dog), HFL (human) and 3T6 (mouse). The 24 h yields in BHK21/C13 cells titrated at 37° C. are shown in Table 2 as are the ratios of the yields of virus grown in a particular cell line compared to the yield in BHK21/C13 cells. It can be seen that 17⁺, 1702 and 1714 essentially behave in a similar fashion; they grow equally well in BHK21/C13, 3T6 and MDCK cells, better in Vero cells and less well in HFL and in BSCI cells. Note that there was no replication defect in the mouse 3T6 cells demonstrating that the lack of growth in vivo was not species specific.

Example 3

Latency Studies

Three week old Balb/c mice were inoculated in the right rear footpad with serial 10 fold dilutions of 17⁺, 1702 and 1714 (4 mice/dose) and were monitored daily for two weeks for signs of illness or death. At 6 weeks post inoculation, surviving mice were dissected as outlined in METHODS (above) and ganglia were separately transferred to microtitre wells containing culture medium. Screening for the presence of infectious virus was carried out every second day post explantation, by transferring an aliquot of culture medium to control BHK21/C13 cells. The cells were then incubated at 37° C. for 2 days before staining and examining for the presence of virus plaques or cpe. The results in Table 3 show that at doses of $10^4$ and $10^5$ pfu of 17°, 20% of explanted ganglie reactivated. However, soon after inoculation one of the $10^4$ pfu and 3 of the $10^5$ pfu infected animals developed hind limb paralysis and had to be killed. Animals were not inoculated with $10^6$ pfu of 17⁺ as they would all have been expected to die. With 1702 infected animals, 5% of ganglia at dose of $10^4$ and $10^5$ pfu reactivated and 17.5% reactivated at the $10^6$ pfu dose. This was clearly less efficient than 17⁺ possibly due to the tk negative phenotype of this variant. With 1714 inoculated animals, no quanglia reactivated from $10^4$ pfu infected animals, only 1/40 (2.5%) reactivated from the $10^5$ pfu infected mice and 2/40 (5%) from the $10^6$ pfu infected animals. Virus first reactivated at day 6 post explantation and there was no significant difference in the timing of reactivation between the 3 viruses. Virus reactivation was confined to the lumbar ganglia in the 3 groups of mice.

Taking into account the tk negative phenotype, the variant 1714, although capable of latency, was much less efficient than 1702 in establishing the latent state and/or reactivating from it following explantation.

Example 4

Introduction of the 1714 deletion into the 17⁺ wild type genome

As the 1714 deletion was not in a wild type background ie the four Xbal sites of 0.07, 0.29, 0.45 and 0.63 mu were deleted in the genome and the virus was tk negative, it was conceivable that its avirulent phenotype was at least in part due to these other mutations. It seemed very unlikely as the parent strain 1702, which contains the same Xbal negative and tk negative mutations had a virulence phenotype essentially equivalent to 17⁺. Nonetheless we decided to introduce the deletion in 1714 into an otherwise totally wild type genome. 17⁺ DNA was co-transfected with a 10-fold excess of plasmid cloned BamHI k of 1714. Resultant single progeny plaques were isolated and their DNA profiles analysed by the method of Lonsdale (1979). A virus with a 1714 BamHI profile designated 1716 was isolated, plaque purified a further 3 times and a virus stock grown. To confirm that 1716 has retained its wild type background in respect of Xbal sites and tk activity, the DNA of 1716 was digested with Xbal and a tk assay performed. It was found that 1716 had a normal wild type Xbal profile retaining the four sites in $U_L$ whereas 1714 and 1702 fail to digest with Xbal. The results of the tk assay for 1716 compared to 17⁺, 1702 and 1714 are given in Table 4 and demonstrate that 1716 is as efficient as 17⁺ in synthesising tk. The neurovirulence phenotype of 1716 was tested by IC inoculation of Balb/c mice. Its $LD_{50}$ value compared to 17⁺ and 1714 is shown in Table 5. It can be seen that it is non-neurovirulent with an $LD_{50}$ value of $7 \times 10^6$ pfu/mouse while in this experiment 17⁺ had an $LD_{50}$ value of <10 pfu/mouse confirming that the sequences deleted in 1716 confer neurovirulence on strain 17.

Results of a single cycle growth experiment with 1716 showed that 1716 grows as efficiently as wild type 17⁺ virus.

TABLE 1

| | Intracerebral (IC) inoculum/mouse (pfu) | | | | | | |
|---|---|---|---|---|---|---|---|
| Virus | $10^2$ | $10^3$ | $10^4$ | $10^5$ | $10^6$ | $10^7$ | $LD_{50}$ (pfu/mouse) |
| 17⁺ | 4/4* | 4/4 | ND | ND | ND | ND | <$10^{1.5}$ |
| 1702 | 2/4 | 3/4 | 4/4 | 4/4 | ND | ND | $5 \times 10^2$ |
| 1714 | ND | 0/4 | 0/4 | 0/4 | 0/4 | 3/4 | $7 \times 10^6$ |

*Number dead/Number inoculated
ND = Not done

TABLE 2

| Cell type Virus | BHK21/C13 standard | Vero | BSC1 | 3T6 | MDCK | HFL |
|---|---|---|---|---|---|---|
| 17⁺ | $7.6 \times 10^{6*}$ | 1.83⁺ | 0.43 | 0.98 | 0.68 | 0.65 |
| 1702 | $5.2 \times 10^6$ | 2.8 | 0.48 | 1.31 | 1.11 | 0.29 |
| 1714 | $5.6 \times 10^6$ | 1.34 | 0.39 | 0.97 | 1.07 | 0.42 |

*Virus yield over 24 h at 37° C. expressed as pfu/5 × $10^5$ cells
⁺Ratio of yield of virus in the particular cell type compared to the yield in BHK21/C13 cells.

TABLE 3

| Inoculating dose Virus | $10^4$ pfu/mouse | $10^5$ | $10^6$ |
|---|---|---|---|
| 17+ | 6/30* (20⁺) | 2/10 (20)⁺⁺ | ND |
| 1702 | 2/40 (5) | 2/40 (5) | 7/40 (17.5) |
| 1714 | 0/40 (0) | 1/40 (2.5) | 2/40 (5) |

*No. of ganglia reactivating/No of ganglia explanted
⁺% of reactivating ganglia
⁺⁺Four animals were infected/dose and 10 ganglia explanted from each. With 17⁺ infected animals, 1 animal at $10^4$ pfu and 3 at $10^5$ pfu dose developed paralysis soon after infection and had to be killed.

TABLE 4 tk assays on Glasgow strain 17 and the variants 1714 and 1716

| | Radioactivity cpm/μg protein |
|---|---|
| Mock infected | 11267 |
| Glasgow strain 17 | 143894 |
| 1714 | 8399 |
| 1716 | 131987 |

TABLE 5

| | Intracerebral (IC) inoculum/mouse (pfu) | | | | | | | |
|---|---|---|---|---|---|---|---|---|
| Virus | $10^1$ | $10^2$ | $10^3$ | $10^4$ | $10^5$ | $10^6$ | $10^7$ | $LD_{50}$ (pfu/mouse) |
| 17+ | 4/4* | 4/4 | ND | ND | ND | ND | ND | <10 |
| 1714 | ND | ND | ND | ND | 0/4 | 0/4 | 1/4 | $5 \times 10^6$ |
| 1716 | ND | ND | ND | 0/4 | 0/4 | 0/4 | 3/4 | $7 \times 10^6$ |

*No. dead/No. inoculated
ND = Not done

Example 5
Construction of HSV-1 1716 gD1+, gD2+.

A recombinant plasmid containing the Hind III 1 fragment of HSV 2 strain HG52 (McGeoch et al 1987a) was digested with restriction endonucleases Bst EII and Dra I and a 3 Kb fragment from the Dra I site at np 5893 to the BSt EII site at np 8893 purified. This fragment contains the promoters, open reading frames and poly A signal of the 3' coterminal genes UL6 (gD-2) and US7 (gI-2). The 5' overhang of the Bst EII site was blunt ended using klenow polymerase. This gD-2 containing fragment was inserted into a Bam HI/ECoR1 91610/96751 np fragment of HSV1 containing UL43 (McGeoch et al 1988) a non-essential integral membrane protein (Maclean C et al 1991). The site of insertion was a unique Nsi I site np 94911 at the 5' end of UL43. The 5' overhang of the Nsi I site was blunt ended using klenow polymerase. All cloning techniques are as described by Maniatis et al 1982.

The recombinant UL43 gD2 HSV1 fragment was cotransfected with intact HSV1 1716 variant DNA and recombinant genomes isolated as described (Example 4 and Maclean et al 1991). A HSV recombinant containing gD2 was isolated. This virus gD1+ gD2+, ICP34.5- is known as 1761.

Example 6
a) Construction of HSV-1 1716 UL26 ts.

The Cloned ECORI f fragment of ts 1201 (Preston et al 1983) contains the UL 26 gene with a ts point mutation. This was recombined into 1716 to generate HSV-1716 UL26 ts as previously described in example 4.
Construction of HSV-1 1716 gD1+ gD2+ UL26 ts.

b) HSV-1 1716 UL26 ts and HSV-1 1716 gD1+ gD2+ from the above examples is recombined using standard methodology (Brown et al 1973) to give an HSV-1 1716 gD1+ gD,2+, UL26 ts virus.

Example 7
Construction of 1716 gD1+, gD2+ LAT P- and 1716 gD1+, gD2+ UL26 ts LAT P-.

A fragment (Steiner et al 1989, JuneJo et al 1991) isolated from HSV-1 1704 carries a 942 bp deletion in both copies of the LAT promoter. This fragment is cotransfected with 1716 gD1+ gD2+ and 1716 gD1+, gD2+, UL26, DNA and single plaques analysed, to give 1716 gD1+ gD2+ LAT P- and 1716 gD1+ gD2+, UL26 ts, LAT P-

HSV-1 strains 1714 and HSV strains 1716 have been deposited at the European Collection of Animal Cell Cultures, Vaccine Research and Production Laboratories, Public Health Laboratory Services at Porton Down, Salisbury Wiltshire SP4, 0J9, UK on Jan. 28, 1992 and given the accession Numbers V92012802 and V92012803 respectively.

REFERENCES

Ackermann, M., Choi, J., Sarmiento, M., Lerner, R. A. & Roizman, B. (1986). Identification by antibody to a synthetic peptide of a protein specified by a diploid gene located in the terminal repeats of the L component of herpes simplex virus genome. J. Virol. 58, 845–850.

Brown, S. M., Ritchie, D. A. & Subak-Sharpe, J. H. (1973). Genetic studies with herpes simplex virus type 1. The isolation of temperature sensitive mutants, their arrangement into complementation groups and recombination analysis leading to a linkage map. J. Gen. Virol. 18, 329–346.

Brown, S. M. Harland, J. & Subak-Sharpe, J. H. (1984). Isolation of restriction endonuclease site deletion mutants of herpes simplex virus. J. Gen. Virol. 65, 1053–1068.

Brown, S. M. & Harland, J. (1987). Three mutants of herpes simplex virus type 2: one lacking the genes US10, US11 & US12 and two in which $R_S$ has been extended by 6 kb to 0.91 map units with loss of $U_S$ sequences between 0.94 and the $U_S/TR_S$ junction. J. Gen. Virol. 68, 1–18.

Chou, J & Roizman, B. (1986). The terminal 'a' sequence of the herpes simplex virus genome contains the promoter of a gene located in the repeat sequences of the L component. J. Virol. 57, 629–637.

Chou, J & Roizman, B. (1990). The herpes simplex virus I gene for ICP34.5 which maps in inverted repeats is conserved in several limited passage isolates but not in strain 17 syn+. J. Virol. 64, 1014–1020.

Chou, J., Kern, E. R., Whitley, R. J. and Roizman, B. (1990). Mapping of herpes simplex virus-1 neurovirulence to $\gamma_1$ 34.5; a gene nonessential for growth in culture. Science, 250; 1262–1266.

Clements, G. B. & Subak-Sharpe, J. H. (1983). Recovery of herpes simplex virus 1 ts mutants from the dorsal root ganglia of mice. In: Immunology of Nervous System Infections. Progress in Brain Research Vol 59 pp 203–208. Edited by P. O. Baker, V ter Moulen & F. Clifford Rose, Amsterdam Elsevier.

Clements, G. B. & Subak-Sharpe, J. H. (1988). Herpes simplex virus type 2 establishes latency in the mouse footpad. J. Gen. Virol. 69, 375–383.

Harland, J. & Brown, S. M. (1985). Isolation and characterisation of deletion mutants of herpes simplex virus type 2 (Strain HG52). J. Gen. Virol. 66, 1305–1321.

Harland, J. & Brown, S. M. (1985). A herpes simplex virus type 2 variant in which a deletion across the L-S junction is replaced by single or multiple reiterations of extraneous DNA. J. Gen. Virol. 70, 2121–2137.

Jamieson, A. T. & Subak-Sharpe, J. H. (1974). Biochemical studies on the herpes simplex virus specified deoxypyrimidine kinase activity. J. Gen. Virol. 24, 481–492.

JuneJo F, Maclean A. R. & Brown S. M. (1991). Sequence analysis of HSV1 Strain 17 variants 1704, 1705 and 1706 with respect to their origin and effect on the latency associated transcript sequence, J. General Virology 72, 2311–2315.

Lonsdale, D. H. (1979). A rapid technique for distinguishing herpes simplex virus type 1 from type 2 by restriction enzyme technology, Lancet i, 849–852.

Maniatis, T., Fritsch, E. F. & Sambrook, J. (1982). Molecular cloning. A laboratory manual. Cold Spring Harbor Laboratory.

MacLean, A. R. & Brown, S. M. (1987a). Generation of a herpes simplex virus type 1 variant devoid of XbaI sites. J. Gene. Virol. 68, 68 1165–1171.

MacLean, A. R. & Brown, S. M. (1987b). A herpes simplex virus type 1 variant which fails to synthesise the immediate early polypeptide Vmw IE63. J. Gen. Virol. 68, 1339–1350.

MacLean, A. R. & Brown, S. M. (1987c). Deletion and duplication variants around the long repeats of herpes simplex virus strain 17. J. Gen. Virol. 68, 3019–3031.

MacLean, C. A., Efstathiou S., Elliott M. L., Jamieson F. E., & McGeoch D. J. (1991). Investigation of HSV1 genes encoding multiple inserted membrane proteins. J. of Gen. Virol. 72 897–906.

MacPherson, I. & Stoker, M. G. (1962). Polyoma transformation of hamster cell clones—an investigation of genetic factors affecting cell competence. Virology 16, 147–151.

McGeoch, D. J., (1987). The genome of herpes simplex virus: structure, replication and evolution. J. Cell Science, 7 (supplement) 5194–5222.

McGeoch D. J. et al (1987)a) DNA sequence and Genetic content of the Hind III 1 region of the short unique component of the HSV-2 genome: identification of the gene encoding glycoprotein G and evolutionary comparisons. J. Gen Virol 19 38.

McGeoch, D. J., Dalrymple, M. A., Davison, A. J., Colan, A., Frame, M. C., McNab, D., Perry, L. J., Scott, J. E. & Taylor, P. (1988). The complete DNA sequence of the long unique region in the genome of herpes simplex virus type 1. J. Gen. Virol. 69, 1531–1574.

Marsden, H. S., Stow, N. D, Preston, U. G, Timbury, M. C. and Wilkie, N. M. (1978). J. Virology, 28; 624–642.

Liu F P and Roizman B (1991a). The Herpes Simplex Virus 1 Gene encoding a Protease also contains within its conding Domain the Gene Encoding the more abundant Substrate. J. Virology p5149.

Liu F and Roizman B, (1991b) The Promoter, Transcriptional Unit and Coding Sequence of Herpes Simplex Virus 1 family 35 proteins are contined within and in Frame with the $U_L$26 Open Reading Frame, J of Virology p206–212.

Perry, L. J. & McGeoch, D. J. (1988). The DNA sequences of the long repeat region and adjoining parts of the long unique region in the genome of herpes simplex virus type 1. J. Gen. Virol. 69, 2831–2846.

Preston, V. G., Coates J. A.+Rixon F. J. (1983). Identification and characterisation of a herpes simplex virus gene product required for encapisation of virus DNA. J. Virol 45 1056–1064.

What is claimed is:

1. An HSV-1 strain 17, the genome of which is modified in the terminal portion of $R_L$ within Bam H1 s(0–0.02 and 0.81–0.83 mu) such that said HSV 1 strain 17 lacks neurovirulence.

2. An HSV-1 strain as claimed in claim 1 wherein the genome is modified by a deletion.

3. An HSV-1 strain 17 as claimed in claim 1 which is an isolated naturally occurring HSV-1 Strain 17 deletion variant wherein the genome is modified in the terminal portion of $R_L$ within the Bam H1 s(0–0.02 and 0.81–0.83 mu).

4. An HSV-1 strain as claimed in claim 1 in which at least 0.5 to 3 kb of the Bam HI s region and its counterpart in $TR_L$ is deleted.

5. An HSV-1 strain as claimed in claim 1 in which at least 0.7–2.5 Kb of the Bam HI s region and its counterpart in $TR_L$ is deleted.

6. An HSV-1 strain 17 as claimed in claim 1 which is Strain HSV-1 1714.

7. An HSV-1 strain 17 as claimed in claim 1 which is strain HSV-1 1716.

8. An HSV-1 strain as claimed in claim 1 in which the strain has been further modified by incorporating a temperature sensitive mutation into the UL26 gene.

9. An HSV-1 strain as claimed in claim 1 further modified by incorporating a mutation rendering the LAT promoter ineffective.

10. A composition comprising an HSV-1 strain as claimed in claim 1.

* * * * *